(12) United States Patent
Chanana et al.

(10) Patent No.: US 7,705,168 B2
(45) Date of Patent: Apr. 27, 2010

(54) MANUFACTURING PROCESS FOR TIGECYCLINE

(75) Inventors: Gurmukh Chanana, West Nyack, NY (US); Dominic Ventura, Glenmoore, PA (US); Richard Saunders, Palisades, NY (US); Mahdi B. Fawzi, Morristown, NJ (US)

(73) Assignee: Wyeth LLC, Madison, NJ (US)

( * ) Notice: Subject to any disclaimer, the term of this patent is extended or adjusted under 35 U.S.C. 154(b) by 818 days.

(21) Appl. No.: 11/455,144

(22) Filed: Jun. 16, 2006

(65) Prior Publication Data

US 2007/0026080 A1    Feb. 1, 2007

Related U.S. Application Data

(60) Provisional application No. 60/691,173, filed on Jun. 16, 2005.

(51) Int. Cl.
*C07C 237/26* (2006.01)
*A01N 25/26* (2006.01)
*A61K 31/65* (2006.01)

(52) U.S. Cl. .................. 552/203; 424/419; 514/152
(58) Field of Classification Search ........... 424/419; 552/203; 514/152
See application file for complete search history.

(56) References Cited

U.S. PATENT DOCUMENTS

| 3,026,248 | A |  | 3/1962 | Melvin et al. |
| 5,284,963 | A |  | 2/1994 | Sum et al. |
| 5,494,903 | A |  | 2/1996 | Hlavka et al. |
| 5,675,030 | A |  | 10/1997 | Krishnan et al. |
| 6,660,267 | B1 | * | 12/2003 | Carroll .................. 424/181.1 |
| 2003/0236265 | A1 | * | 12/2003 | Sayada .................. 514/252.13 |
| 2006/0094668 | A1 | * | 5/2006 | Raible et al. .................. 514/26 |
| 2006/0247181 | A1 | * | 11/2006 | Fawzi et al. .................. 514/23 |

FOREIGN PATENT DOCUMENTS

WO    WO 2006/130431 A1    12/2006

OTHER PUBLICATIONS

Sum et al., "Synthesis and structure-activity relationship of novel glycylcycline derivatives leading to the discovery of GAR-936.", Bioorganic & Medicinal Chemistry Letters, vol. 9, pp. 1459-1462, 1999.*
Lester A. Mitscher, The Chemistry of the Tetracycline Antibiotics, Chapter 6.3, pp. 172-173, and Chapter 2, pp. 52-54, 1978.
Muralidharan, G. et al., "Pharmacokinetics of tigecycline after single and multiple doses in healthy subjects," Antimicrobial Agents and Chemotherapy, 2005, 49:1, 220-229.
Pawelczyk, E. et al., "Kinetics of Drug Decomposition. Part 74. Kinetics of Degradation of Minocycline in Aqueous Solution," Polish Journal of Pharmacology and Pharmacy, 1982, 34: 5/6, 409-421.
Waterman, K. C., et al., "Stabilization of Pharmaceuticals to Oxidative Degradation," Pharmaceutical Development and Technology, 2002, 7:1, 1-32.
Garrison, M. et al., "Tigecycline: An investigational glycylcycline antimicrobial with activity against resistant gram-positive organisms", Clininical Therapeutics, Excerpta Medica, 2005, 27:1, 12-22.

* cited by examiner

*Primary Examiner*—Barbara P Badio
(74) *Attorney, Agent, or Firm*—Michael P. Straher; Ram W. Sabnis (57) ABSTRACT

Disclosed herein is a manufacturing process for the preparation of tigecycline suitable for intravenous infusion.

11 Claims, 2 Drawing Sheets

MANUFACTURING PROCESS FOR TIGECYCLINE

This application claims priority from provisional application, application No. 60/691,173 filed Jun. 16, 2005 the entire disclosure of which is hereby incorporated by reference.

FIELD OF THE INVENTION

The present invention relates to a manufacturing process for the preparation of tigecycline.

BACKGROUND OF THE INVENTION

Tigecycline is an antibiotic with a broad spectrum of antibacterial activity. Importantly tigecycline is effective against several resistant strains of bacteria. Tigecycline in a powder presentation is reconstituted by the addition of a compatible reconstitution diluent prior to intravenous infusion. The antibiotic tigecycline is a t-butylglycyl substituted naphthacenecarboxamide free base.

Tigecycline is however difficult to manufacture because it is vulnerable to degradation including oxidative degradation from atmospheric oxygen and epimer formation.

There is therefore a need for a manufacturing process which controls epimerization and oxidation of tigecycline in bulk manufacturing.

SUMMARY OF THE INVENTION

The present invention is directed to a manufacturing process for tigecycline by controlling epimer formation and oxidation degradation during the bulk manufacturing of the lyophilized powder presentation. In particular, controlling the temperature and oxygen level during the steps of the process are important features of the invention.

Tigecycline is protected during the process by sparging with an inert gaseous medium comprising a nonreactive gas, such as nitrogen, and control of the temperature.

An embodiment of the invention is to provide the manufacture of tigecycline with total degradants less than 0.9% by controlling the level of dissolved oxygen in conjunction with temperature control of the bulk aqueous solution.

A further embodiment of the invention is to provide a manufacturing process for tigecycline as a reconstitutable powder having less than 0.9% total degradants and to further provide the tigecycline reconstitutable powder from solutions of water for injection (WFI) and tigecycline on at least an 80 L scale.

An embodiment of the invention is to provide a manufacturing process of tigecycline in WFI water at a concentration of about 10 to 50 mg/ml, preferably 20 mg/mL wherein the oxygen level in the water is less than 0.5 ppm by sparging said water with gaseous nitrogen and wherein said solution may be added to vials and the solution in said vials lyophilized to a reconstitutable powder.

An additional embodiment of the invention is to provide a manufacturing process having a total manufacturing hold time for bulk solution of about 13 to about 24 hours for the production of tigecycline powder.

A further embodiment of the invention is to provide tigecycline powder available for reconstitution prior to intravenous administration and having a shelf life of at least 18 months.

An additional embodiment of the invention is to provide a manufacturing process wherein the WFI water is at a temperature of about 2° C. to about 8° C.

A further embodiment of the invention is to provide a maximum sterile holding time from the filling of the first vial to the start of lyophilization cycle of 6 hours.

An embodiment of the invention is to provide a manufacturing process for the production of tigecycline as a reconstitutable powder having less than 0.9% total degradants comprising the steps:

a. reducing and maintaining the oxygen level in WFI water to less than or equal to 0.5 ppm while maintaining the temperature at about 2° C. to about 8° C.;
b. forming a solution of tigecycline in said water of step a at a concentration of about 10 to 50 mg/ml while maintaining said temperature and oxygen level;
c. filling vials with said solution of step b;
d. lyophilizing said solution of step c to form 25 mg to 150 mg of reconstitutable powder in a vial; and
e. sealing said vial under nitrogen.

Preferably a solution of tigecycline in step b of the above described process is at a concentration of about 20 mg/ml.

Preferably 50 mg to 150 mg, more preferably 50 mg of reconstitutable powder is in the vial of step d of the above described process.

Figure 1:
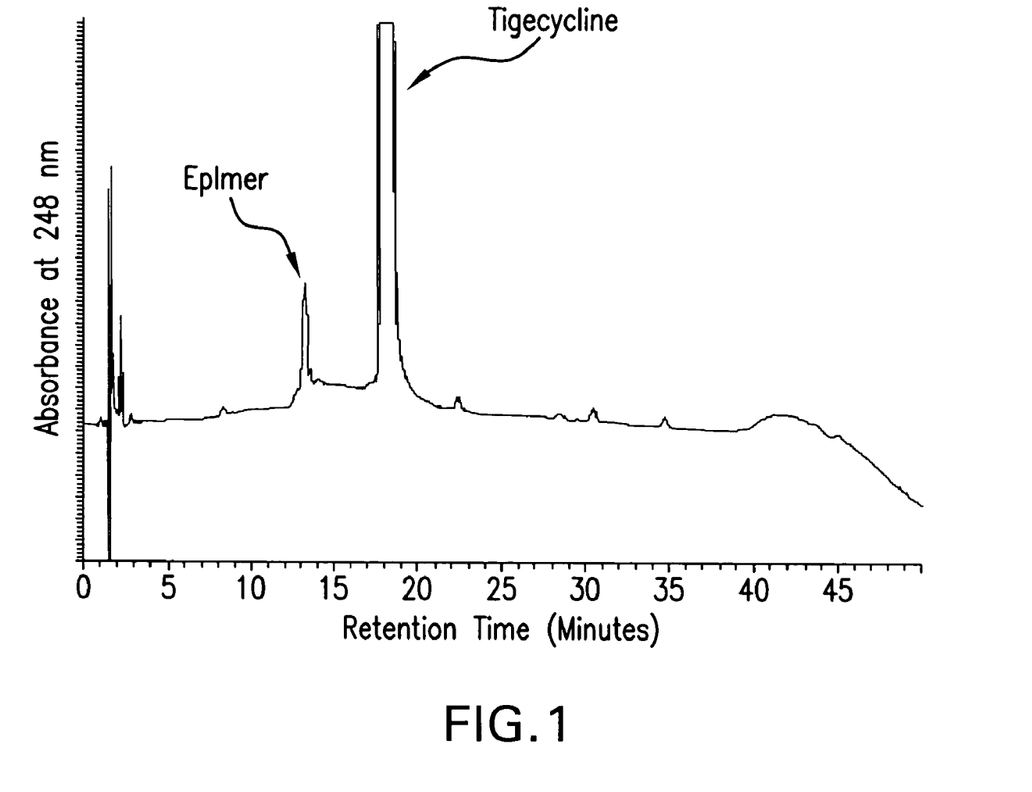
FIG. 1 shows a typical chromatogram of the reverse-phase HPLC elution profile of tigecycline from the manufacturing process.
Figure 2:
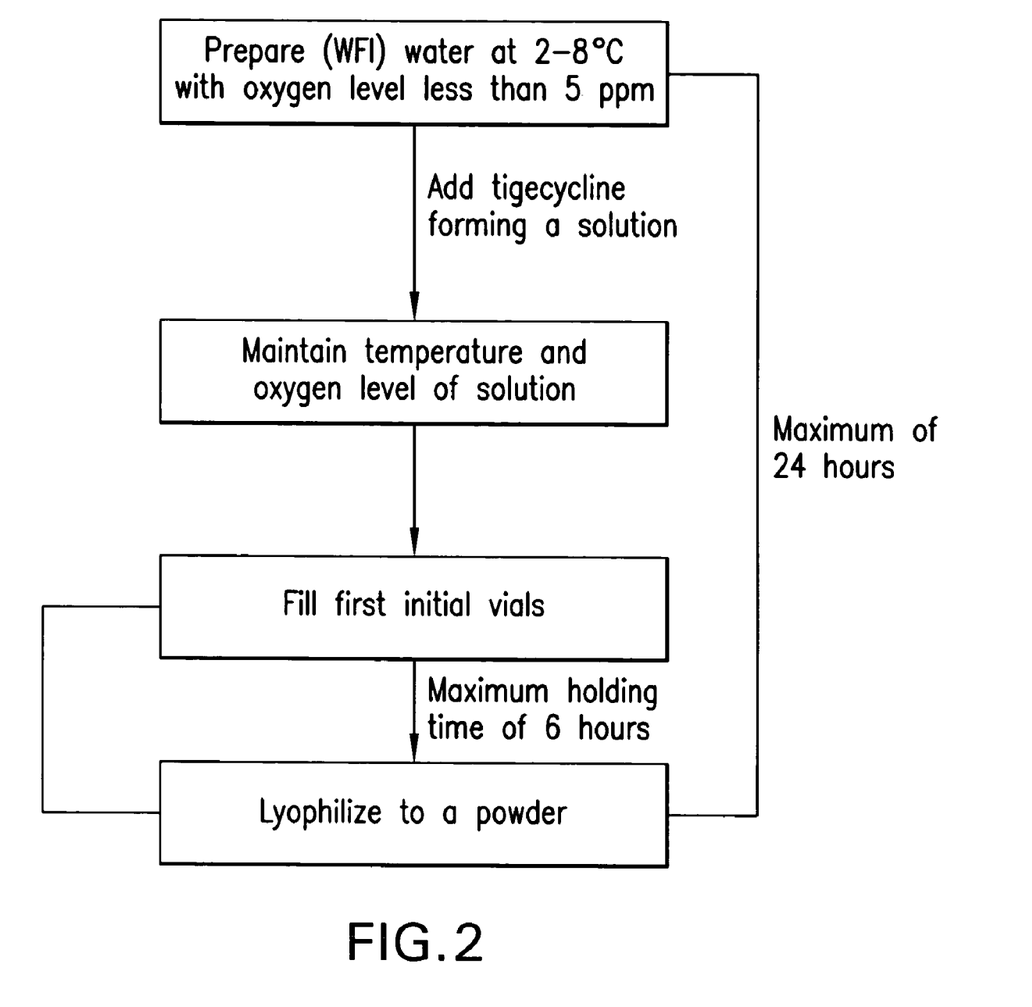
FIG. 2 shows the steps of the tigecycline manufacturing process.

The lyophilized and reconstituted tigecycline powder has been analyzed to have a reverse-phase HPLC elution profile substantially as shown in FIG. 1.

Another embodiment of the present invention is to provide a reconstitutable powder of tigecycline wherein the powder has less than 0.9% total degradants. In a further embodiment the powder has less than 0.5% total degradants.

DETAILED DESCRIPTION OF THE INVENTION

The present invention provides a manufacturing process for tigecycline as a reconstitutable powder having less than 0.9% total degradants. The process to prepare the tigecycline reconstitutable powder may be provided from solutions of water for injection (WFI) and tigecycline on an 80 L scale or greater than an 80 L scale.

By total degradants, we mean compounds or products that are the result of degradation of tigecycline, including those formed due to oxidation of tigecycline (for example at the C-11 position forming a hydroxyl group or at the C-6 position followed by dehydration to form a 6-ene product), or those compounds or products formed due to secondary reactions (e.g. decarboxylation, hydrolysis, photoreactions or ring closures) (for example those products formed due to photo-induced reaction through hydrolysis and deamination at C-4 position). Included in the definition is epimer. Excluded from the definition are minocycline and 9-amino minocycline.

By "less than 0.9% total degradants", we mean the ratio of total degradants to tigecycline is less than 0.9% at 24 hours after forming the solution of tigecycline, but prior to lyophilization.

Generally the process provides a solution of tigecycline in WFI water at a concentration of about 10 to 50 mg/ml, preferably 20 mg/mL wherein the oxygen level in the water is less than 0.5 ppm by sparging said water with gaseous nitrogen and wherein said solution may be added to vials and the solution is said vials lyophilized to a reconstitutable powder.

The invention provides a manufacturing process having a total manufacturing hold time for the bulk solution of about 13 to about 24 hours for the production of tigecycline powder available for reconstitution and further having a shelf life of at least 18 months.

The invention provides a manufacturing process wherein the WFI water is held at a temperature of about 2° C. to about 8° C. and the water is further sparged with nitrogen so the oxygen level is below 5 ppm.

A maximum sterile holding time from the filling of the first vial with bulk solution to the start of lyophilization cycle of 6 h has been developed to ensure control of degradation.

The invention provides a manufacturing process for the production of tigecycline as a reconstitutable powder having less than 0.9% total degradants by first reducing and maintaining the oxygen level in WFI water to less than 0.5 ppm while maintaining the temperature at about 2° C. to about 8° C. before adding tigecycline and forming a solution at about 10 to 50 mg/ml while still maintaining the temperature and oxygen level. The solution of tigecycline in water can be added to vials and further lyophilized to a reconstitutable powder and the vial further sealed under nitrogen.

Preferably the solution of tigecycline is at 20 mg/ml and the vial has about 50 mg of reconstitutable powder following lyophilization.

EXAMPLES

The following examples represent the process of the invention and are presented for purposes of illustration only. While the invention has been described in detail and with reference to specific embodiments, it will be apparent to one skilled in the art that various changes and modifications may be made to such embodiments without departing from the spirit and scope of the invention.

The following describes a typical manufacturing process for Tigecycline for Injection for a typical batch size of 80 L.

Non-Sterile Bulk Formulation Stage
1. Before starting bulk formulation stage, purge with filtered nitrogen the formulation and filling lines, product transfer line and the formulation, intermediate and holding tanks.
2. Add approximately 95% (76 L) of required amount of Water for Injection in the formulation tank and chill the water to 2° C.-8° C. while sparging with filtered nitrogen, until the dissolved oxygen content is ≦0.5 mg/L (ppm).
3. Measure the dissolved oxygen content of the water. If the dissolved oxygen content is greater than 0.5 mg/L, continue to sparge the water with filtered nitrogen until dissolved oxygen content is ≦0.5 mg/L (ppm), and the temperature is 2° C.-8° C.
4. Continue sparging and pressurize the holding tank with filtered nitrogen. Discontinue sparging of the water in the formulation tank prior to adding the drug substance and continue with a filtered nitrogen blanket.
5. Add 1600 g of drug substance to the tank ensuring that the drug substance is not exposed to air by maintaining filtered nitrogen flow during the entire process.
6. Mix the bulk solution. The solution temperature must be 2° C.-8° C.
7. Add Water for Injection to formulation tank until the final volume/weight (80 L) is reached and mix the solution.
8. Maintain a filtered nitrogen blanket in the formulation tank. Measure the dissolved oxygen content.
9. If the dissolved oxygen content of the solution is more than 0.5 mg/L, continue filtered nitrogen sparging until a stable dissolved oxygen content measure is obtained.

Aseptic Filtration and Filling
1. Fill into sterilized glass vials and check fill weight periodically. Partially stopper the vials. This process should be completed with 6 hours (Maximum allowable sterile solution hold time)
2. Load trays with partially stoppered vials from the filling machine. Place the filled trays in closed transport carts.
3. The manufacturing process up to this step should be completed with 13-24 hours (Maximum allowable Bulk solution hold time)

Lyophilization
1. Set shelf inlet temperature to 2° C. (±5° C.).
2. Load the vials.
3. Close the freeze dryer door to start the cycle.
4. Reduce the shelves inlet temperature to −45° C. Hold at shelf inlet temperature of −45° C. (±5° C.) for up to 4 hours or until product temperature of −17° C. or below is achieved.
5. Reduce chamber pressure to 150 mTorr (mT)±150 mT prior to start the Primary Drying Stage.'
6. Start Primary Drying, and continue for up to 20 hours (shelf temperature: −10° C. to +25° C.) or until the product temperature rises above 0° C., by increasing the shelf temperature to restrict product temperature below the collapse temperature (−6.5° C.)/eutectic temperature (−0.74° C.) of the product.
7. Perform Terminal Drying by increasing the shelf inlet temperature to 40° C. (±5° C.) and hold up to 9 hours or until the product temperature is maintained at >30° C. for at least 3 hours.
8. Break to a partial vacuum of 12.5 psi (±0.5 psi) with filtered nitrogen and completely stopper the vials.
9. Break partial vacuum to atmospheric pressure.
10. Remove the vials from the dryer and crimp-seal.

HPLC Testing

The contents of the sample vials are dissolved in diluent. The sample solution is diluted, if necessary, and chromatographed on a reversed phase column using gradient elution. Impurities are determined by comparing the impurity peak areas in the sample preparation chromatogram to the average area of tigecycline peaks in the standard preparation chromatograms obtained concomitantly.

Chromatographic Column—Length about 15 cm, inside diameter about 4.6 mm, packed with Inertsil ODS2, 5 μm size particles or equivalent.

Detector—Ultraviolet spectrophotometric detector capable of operating at 248 nm with a sensitivity of about 0.5 absorbance units full scale.

Reagents and Materials

Acetonitrile—HPLC grade.

Water—Suitable for HPLC.

Phosphoric Acid—Reagent grade, approx. 87% H3PO4.

Potassium Hydroxide Solution (1N)—Reagent grade.

Trifluoroacetic Acid—Reagent grade.

Dibasic Potassium Phosphate—K2HPO4, HPLC grade.

Sodium EDTA—(Ethylenedinitrilo)—Tetraacetic Acid Disodium Salt—HPLC grade.

Sodium Bisulfite—NaHSO3, Reagent grade.

Mobile Phase A—Dissolve 4.35 g of dibasic potassium phosphate and 0.93 g of sodium.

EDTA in 950 mL of water. Adjust pH to 6.4 with phosphoric acid. Add 50 mL of acetonitrile and mix well. Filter through a 0.45 µm pore size membrane filter, if necessary. Degas, if necessary.

Mobile Phase B—Dissolve 4.35 g of dibasic potassium phosphate and 0.93 g of sodium.

EDTA in 500 mL of water. Adjust pH to 6.4 with phosphoric acid. Add 500 mL of acetonitrile and mix well. Filter through a 0.45 µm pore size membrane filter, if necessary. Degas, if necessary.

Diluent—Weigh 4.35 g of dibasic potassium phosphate and 0.50 g of sodium bisulfite into a one liter volumetric flask. Dissolve and dilute to volume with water. Adjust the pH of this solution to 8.0 with 1N potassium hydroxide.

EDTA Solution—Weigh 3.7 g of sodium EDTA into a one liter volumetric flask. Dissolve with 950 mL water. Add 50 mL acetonitrile and mix well.

Tigecycline Reference Standard—Of known strength (S).

The results of additional studies to investigate the effect of processing parameters such as temperature, time, and dissolved oxygen content on the purity profile of tigecycline solutions using the following materials, methods and procedures are presented in Tables A to O.

Materials and Methods
Tigecycline Drug Substance Lot # 871858C
0.1N NaOH Lot #9712031
0.1N HCl Lot # 2853
Sterile Water For Injection Lot # J3N472 (B. Braun)

Procedure

The experiments were run in plastic glove bags under normal laboratory light conditions. Plastic glove boxes will be used to control the headspace of the beakers. The batch size was 200 mL.

1. Prepare the glove bag with a mixture of nitrogen and air to achieve an oxygen level in the solution as per the design.
2. Place the jacketed beaker on the magnetic stirrer. Connect it to the cooler. Set the cooler to the desired set point.
3. Add 200 mL of SWFI in to the beaker. Allow equilibrating. Measure the temperature and oxygen content. When it reaches the desired condition, add accurately weighed API and mix until dissolved. If necessary use spatula to aid dissolution. For pH adjustments, use 4 mL of either 0.1N NaOH or 0.1N HCl and 196 mL of WFI for manufacture.
4. After complete dissolution, Transfer about 5.5 mL of Solution in vials and stopper them. These vials will be stoppered at the appropriate headspace conditions. Place the vials in appropriate temperature conditions.
5. Sample the vials at 1, 4, 8, 10, 12 and 24 hours. Send the samples for analysis. Freeze the 10, 12 and 24 samples at −20° C. for analysis the following day.
6. Measure pH and record color of the solution at each time point.

Results

Experimental Conditions

The 1-hour samples were taken directly from the beakers. Samples for later time points were collected in stoppered vials processed in the atmosphere of the bag in order to simulate the headspace conditions then placed in water baths or refrigerator to maintain there respective temperature conditions. This was done to maintain safety in the lab. Disposable plastic glove bags require constant flow of a mixture of nitrogen and air to maintain headspace oxygen level that will result in the desired dissolved oxygen (DO) content in the sample. The pH of samples was measured at each sample points.

Strength and Degradation Profile

Strength and degradation profile was analyzed by HPLC as described above. The results show that when oxygen is removed from the process and the temperature is controlled, very little degradation is seen. Degradation was slightly higher at higher temperature condition.

The results of these additional studies show that when oxygen is removed from the process, very little degradation is seen (see runs H, I, and K-O). Degradation was slightly higher at higher temperature condition. The range of pH (7.7-8.2) studied did not have any significant effect on the degradation of tigecycline bulk solution however, a slightly higher degradation was seen for sample at pH 8.2, temperature of 8° C. and 2 ppm dissolved oxygen when compared to solution at pH 7.7 and similar temperature and dissolved oxygen content. The total amount of degradation after 24 hours shows an interaction between temperature and the dissolved oxygen level in the solution. The total amount of degradation components found is minimized when the oxygen level is between 0 and about 0.4 ppm regardless of the temperature that the bulk solution was prepared or held at. From an oxygen level of 0.4 ppm to 1.2 ppm—the total amount of degradation products can still be minimized as long as the temperature the bulk solution is produced and held at is lowered from 4° C. to 2° C. as the oxygen level increases. As shown in comparative Runs A-G and J unexceptable degradant levels are found.

| | | \multicolumn{7}{c}{RRT} | | |
|---|---|---|---|---|---|---|---|---|
| Hours | Strength (mg/mL) | MW = 633 0.12 | MW = 572 0.23 | MW = 601 0.50 | MW = 583 0.55 | 0.58 | 9-Amino 0.64 | Epimer 0.74 |
| 1 | 19.639 | BRL | BRL | BRL | BRL | 0.07 | BRL | 0.18 |
| 4 | 19.610 | BRL | BRL | BRL | 0.10 | 0.06 | BRL | 0.20 |
| 8 | 19.473 | BRL | 0.07 | BRL | 0.17 | 0.06 | BRL | 0.19 |
| 10 | 19.806 | BRL | 0.18 | 0.07 | 0.21 | 0.07 | BRL | 0.25 |
| 12 | 19.901 | 0.05 | 0.19 | 0.08 | 0.19 | 0.06 | BRL | 0.26 |
| 24 | 19.504 | BRL | 0.34 | 0.15 | 0.28 | 0.07 | BRL | 0.23 |

Run #A: Tigecycline 20 mg/mL, (Temperature 2° C., pH 8.2, Oxygen = 2.0 mg/L)

-continued

Run #A: Tigecycline 20 mg/mL, (Temperature 2° C., pH 8.2, Oxygen = 2.0 mg/L)

| | | | | | | RRT | | | | |
|---|---|---|---|---|---|---|---|---|---|---|
| Hours | 0.76 | MW = 557 0.78 | Mino 1.64 | MW = 556 1.67 | MW = 597 1.85 | 1.12 | 1.45 | 1.58 | Total | |
| 1 | BRL | BRL | 0.10 | BRL | 0.06 | BRL | 0.06 | BRL | 0.47 | |
| 4 | 0.06 | BRL | 0.10 | 0.09 | 0.08 | BRL | 0.08 | BRL | 0.76 | |
| 8 | BRL | BRL | 0.10 | 0.14 | 0.07 | BRL | 0.07 | BRL | 0.86 | |
| 10 | BRL | 0.06 | 0.10 | 0.18 | 0.08 | BRL | 0.08 | BRL | 1.26 | |
| 12 | 0.06 | 0.06 | 0.10 | 0.19 | 0.08 | BRL | 0.08 | BRL | 1.40 | |
| 24 | 0.06 | 0.08 | 0.11 | 0.29 | 0.14 | BRL | 0.09 | BRL | 1.86 | |

RRT is the relative retention (in column chromatography): ratio of the net retention volume (time) of a component relative to a standard under identical conditions.
BRL means below reporting limit (meaning less than 0.05% of tigecycline peak)

Run #B: Tigecycline 20 mg/mL, (Temperature 8° C., pH 8.2, Oxygen = 2.0 mg/L)

| | | | | | RRT | | | | | | |
|---|---|---|---|---|---|---|---|---|---|---|---|
| Time (Hrs) | Strength (mg/ml) | 0.09 | 0.10 | MW = 633 0.12 | MW = 570 0.14 | MW = 572 0.23 | 0.36 | MW = 601 0.50 | MW = 583 0.55 | 0.58 | 9-Amino 0.64 |
| 1 | 19.149 | BRL | BRL | BRL | BRL | BRL | BRL | BRL | 0.11 | 0.07 | BRL |
| 4 | 19.046 | BRL | BRL | BRL | BRL | 0.15 | BRL | 0.08 | 0.20 | 0.06 | BRL |
| 8 | 18.795 | BRL | BRL | BRL | 0.07 | 0.36 | BRL | 0.17 | 0.27 | 0.06 | BRL |
| 10 | 19.144 | 0.10 | 0.10 | 0.14 | BRL | 0.55 | 0.06 | 0.25 | 0.32 | BRL | BRL |
| 12 | 18.668 | 0.12 | 0.14 | 0.21 | BRL | 0.62 | 0.06 | 0.27 | 0.29 | BRL | BRL |
| 24 | 17.784 | 0.23 | 0.19 | 0.40 | 0.06 | 1.46 | 0.14 | 0.62 | 0.42 | BRL | 0.06 |

| | | | | | | RRT | | | | | |
|---|---|---|---|---|---|---|---|---|---|---|---|
| Time (Hrs) | Epimer 0.74 | 0.76 | MW = 557 0.78 | MW = 528 1.25 | Mino 1.64 | MW = 556 1.67 | MW = 597 1.85 | 2.25 | 1.45 | All Others | Total |
| 1 | 0.20 | BRL | BRL | BRL | 0.10 | 0.14 | 0.08 | BRL | 0.07 | BRL | 0.75 |
| 4 | 0.19 | BRL | BRL | BRL | 0.05 | 0.25 | 0.07 | BRL | 0.07 | BRL | 1.12 |
| 8 | 0.23 | 0.06 | 0.07 | BRL | 0.07 | 0.35 | 0.07 | BRL | 0.07 | BRL | 1.85 |
| 10 | 0.22 | BRL | 0.07 | 0.08 | 0.11 | 0.29 | 0.09 | BRL | BRL | BRL | 2.38 |
| 12 | 0.24 | BRL | 0.08 | 0.11 | 0.09 | 0.23 | 0.08 | BRL | 0.07 | BRL | 2.61 |
| 24 | 0.23 | 0.05 | 0.16 | 0.25 | 0.11 | 0.50 | 0.11 | 0.12 | 0.06 | 0.19 | 5.36 |

Run #C Tigecycline 20 mg/mL (Temperature 2° C., pH 7.7 Oxygen = 2 mg/L)

| | | | | RRT | | | | |
|---|---|---|---|---|---|---|---|---|
| Hours | Strength (mg/mL) | MW = 633 0.12 | MW = 572 0.23 | MW = 601 0.50 | MW = 583 0.55 | 0.58 | 9-Amino 0.64 | Epimer 0.74 |
| 1 | 19.339 | BRL | BRL | BRL | BRL | 0.08 | BRL | 0.20 |
| 4 | 19.246 | BRL | BRL | BRL | 0.08 | 0.06 | BRL | 0.19 |
| 8 | 19.031 | BRL | 0.05 | BRL | 0.14 | 0.06 | BRL | 0.19 |
| 10 | 19.415 | BRL | 0.15 | 0.06 | 0.23 | 0.06 | BRL | 0.27 |
| 12 | 19.048 | BRL | 0.17 | 0.07 | 0.21 | 0.07 | BRL | 0.30 |
| 24 | 19.226 | BRL | 0.30 | 0.14 | 0.28 | 0.05 | BRL | 0.21 |

| | | | | | RRT | | | | |
|---|---|---|---|---|---|---|---|---|---|
| Hours | 0.76 | MW = 557 0.78 | Mino 1.64 | MW = 556 1.67 | MW = 597 1.85 | 1.12 | 1.45 | 1.58 | Total |
| 1 | 0.08 | BRL | 0.10 | BRL | 0.06 | BRL | 0.07 | BRL | 0.59 |
| 4 | BRL | BRL | 0.09 | 0.05 | 0.06 | BRL | 0.07 | BRL | 0.60 |
| 8 | BRL | BRL | 0.11 | 0.14 | 0.07 | BRL | 0.13 | BRL | 0.87 |
| 10 | BRL | BRL | 0.10 | 0.17 | 0.08 | BRL | 0.07 | BRL | 1.20 |
| 12 | 0.05 | 0.06 | 0.10 | 0.20 | 0.08 | BRL | 0.07 | BRL | 1.38 |
| 24 | BRL | BRL | 0.09 | 0.27 | 0.07 | BRL | 0.06 | 0.07 | 1.52 |

| Run #D: Tigecycline 20 mg/mL, (Temperature 8° C., pH 7.7, Oxygen = 2.0 mg/L | | | | | | | | | | | |
|---|---|---|---|---|---|---|---|---|---|---|---|
| | | | | | | RRT | | | | | |
| Time (Hrs) | Strength (mg/ml) | 0.09 | 0.10 | MW = 633 0.12 | MW = 572 0.23 | 0.36 | MW = 601 0.50 | MW = 583 0.55 | 0.58 | 9-Amino 0.64 | Epimer 0.74 |
| 1 | 19.168 | BRL | BRL | BRL | BRL | BRL | BRL | 0.08 | 0.06 | BRL | 0.19 |
| 4 | 18.918 | BRL | BRL | BRL | 0.10 | BRL | 0.06 | 0.16 | 0.05 | BRL | 0.18 |
| 8 | 18.915 | BRL | BRL | BRL | 0.23 | BRL | 0.12 | 0.23 | 0.05 | BRL | 0.19 |
| 10 | 19.292 | BRL | 0.12 | 0.09 | 0.45 | 0.06 | 0.21 | 0.27 | 0.05 | BRL | 0.25 |
| 12 | 18.728 | BRL | 0.19 | 0.14 | 0.55 | 0.06 | 0.24 | 0.29 | BRL | BRL | 0.24 |
| 24 | 18.050 | 0.09 | 0.18 | 0.28 | 1.14 | 0.11 | 0.53 | 0.36 | 0.05 | BRL | 0.27 |

| | | | | | RRT | | | | | | |
|---|---|---|---|---|---|---|---|---|---|---|---|
| Time (Hrs) | 0.76 | MW = 557 0.78 | MW = 528 1.25 | Mino 1.64 | MW = 556 1.67 | MW = 597 1.85 | 2.25 | 1.45 | 1.58 | All Others | Total |
| 1 | BRL | BRL | BRL | 0.08 | 0.10 | 0.08 | BRL | 0.07 | BRL | BRL | 0.65 |
| 4 | BRL | BRL | 0.05 | (<0.05) | 0.21 | 0.08 | BRL | 0.19 | BRL | BRL | 1.09 |
| 8 | BRL | BRL | BRL | 0.11 | 0.37 | 0.14 | BRL | 0.06 | 0.06 | BRL | 1.57 |
| 10 | 0.05 | 0.09 | 0.06 | 0.10 | 0.24 | 0.08 | BRL | 0.07 | BRL | 0.07 | 2.27 |
| 12 | BRL | 0.07 | 0.10 | 0.08 | 0.28 | 0.09 | BRL | 0.10 | BRL | 0.05 | 2.47 |
| 24 | BRL | 0.15 | 0.19 | 0.09 | 0.51 | 0.10 | 0.15 | 0.07 | BRL | 0.05 | 4.32 |

| Tigecycline 20 mg/mL, Run #E, (5° C. Temperature, Oxygen = 2.0 mg/mL) | | | | | | | | | |
|---|---|---|---|---|---|---|---|---|---|
| | | | | | RRT | | | | |
| Time (Hrs) | Strength (mg/mL) | 0.09 | 0.10 | MW = 633 0.12 | MW = 570 0.14 | MW = 572 0.23 | 0.36 | MW = 601 0.50 | MW = 583 0.55 |
| 1 | 19.261 | BRL | BRL | BRL | BRL | BRL | BRL | BRL | 0.07 |
| 4 | 19.215 | BRL | BRL | BRL | BRL | 0.08 | BRL | BRL | 0.17 |
| 8 | 18.970 | BRL | BRL | BRL | 0.06 | 0.26 | BRL | 0.12 | 0.22 |
| 12 | 18.475 | 0.07 | 0.12 | 0.11 | BRL | 0.61 | BRL | 0.33 | 0.33 |
| 24 | 17.950 | 0.10 | 0.16 | 0.17 | 0.10 | 0.99 | 0.08 | 0.46 | 0.43 |

| | | | | | RRT | | | | | |
|---|---|---|---|---|---|---|---|---|---|---|
| Time (Hrs) | 0.58 | Epimer 0.74 | 0.76 | MW = 528 1.25 | Mino 1.64 | MW = 556 1.67 | MW = 597 1.85 | 2.25 | 1.45 | All Others | Total |
| 1 | 0.08 | 0.16 | 0.05 | BRL | 0.09 | 0.08 | 0.08 | BRL | 0.08 | BRL | 0.67 |
| 4 | 0.07 | 0.17 | 0.05 | BRL | 0.10 | 0.16 | 0.07 | BRL | 0.08 | BRL | 0.96 |
| 8 | 0.07 | 0.19 | 0.11 | BRL | 0.10 | 0.26 | 0.09 | BRL | 0.10 | BRL | 1.58 |
| 12 | 0.07 | 0.24 | 0.12 | 0.23 | 0.07 | 0.39 | 0.11 | 0.28 | 0.08 | BRL | 3.15 |
| 24 | 0.05 | 0.28 | 0.13 | 0.27 | BRL | 0.44[a] | 0.12 | 0.33 | 0.07 | 0.07 | 4.23 |

[a] Mino is co-eluting

| Tigecycline 20 mg/mL, Run #F, (2° C. Temperature, Oxygen = 1.0 mg/mL) | | | | | | | | | | | | |
|---|---|---|---|---|---|---|---|---|---|---|---|---|
| | | | | | | RRT | | | | | | |
| Time (Hrs) | Strength (mg/ml) | MW = 570 0.14 | MW = 572 0.23 | MW = 601 0.50 | MW = 583 0.55 | 0.58 | Epimer 0.74 | 0.76 | Mino 1.64 | MW = 556 1.67 | MW = 597 1.85 | 1.45 | Total |
| 1 | 18.733 | BRL | BRL | BRL | BRL | 0.08 | 0.15 | BRL | 0.10 | BRL | 0.07 | 0.07 | 0.47 |
| 4 | 18.700 | BRL | BRL | BRL | 0.10 | 0.07 | 0.16 | BRL | 0.09 | 0.12 | 0.09 | 0.07 | 0.71 |
| 8 | 18.729 | BRL | 0.09 | 0.06 | 0.13 | 0.08 | 0.17 | 0.07 | 0.10 | 0.14 | 0.08 | 0.09 | 1.00 |
| 12 | 18.543 | BRL | 0.13 | 0.07 | 0.16 | 0.07 | 0.18 | 0.06 | 0.09 | 0.15 | 0.09 | 0.08 | 1.07 |
| 24 | 18.818 | 0.08 | 0.29 | 0.12 | 0.21 | 0.07 | 0.19 | 0.06 | 0.10 | 0.16 | 0.08 | 0.07 | 1.43 |

| Tigecycline 20 mg/mL, Run #G, (5° C. Temperature, Oxygen = 1.0 mg/mL) | | | | | | | |
|---|---|---|---|---|---|---|---|
| | | | | RRT | | | |
| Time (Hrs) | Strength (mg/ml) | MW = 570 0.14 | MW = 572 0.23 | 0.36 | MW = 601 0.50 | MW = 583 0.55 | 0.58 | Epimer 0.74 |
| 1 | 18.577 | BRL | BRL | BRL | BRL | BRL | 0.08 | 0.16 |
| 4 | 18.694 | BRL | 0.07 | BRL | BRL | 0.10 | 0.07 | 0.17 |
| 8 | 18.487 | BRL | 0.17 | BRL | 0.09 | 0.13 | 0.07 | 0.18 |
| 12 | 18.507 | BRL | 0.27 | BRL | 0.13 | 0.16 | 0.07 | 0.20 |
| 24 | 18.587 | 0.09 | 0.52 | 0.06 | 0.23 | 0.18 | 0.08 | 0.21 |

| | | | RRT | | | | |
|---|---|---|---|---|---|---|---|
| Time (Hrs) | 0.76 | MW = 528 1.25 | Mino 1.64 | MW = 556 1.67 | MW = 597 1.85 | 2.25 | 1.45 | Total |
| 1 | BRL | BRL | 0.11 | 0.08 | 0.08 | BRL | 0.08 | 0.58 |
| 4 | BRL | BRL | 0.07 | 0.14 | 0.08 | BRL | 0.08 | 0.78 |
| 8 | 0.05 | BRL | 0.11 | 0.17 | 0.09 | BRL | 0.07 | 1.12 |
| 12 | 0.06 | BRL | 0.07 | 0.20 | 0.09 | BRL | 0.09 | 1.34 |
| 24 | 0.10 | 0.05 | 0.11 | 0.23 | 0.10 | 0.07 | 0.08 | 2.09 |

| Run #H: Tigecycline 20 mg/mL, (Temperature 5° C., pH 7.9, Oxygen = 1.0 mg/L) | | | | | | | |
|---|---|---|---|---|---|---|---|
| | | | | RRT | | | |
| Time (Hrs) | Strength (mg/mL) | MW = 633 0.12 | MW = 572 0.23 | MW = 601 0.50 | MW = 583 0.55 | 0.58 | 9-Amino 0.64 | Epimer 0.74 |
| 1 | 19.457 | BRL | BRL | BRL | BRL | 0.09 | BRL | 0.19 |
| 4 | 19.441 | BRL | BRL | BRL | BRL | 0.09 | BRL | 0.20 |
| 8 | 19.361 | BRL | BRL | BRL | BRL | 0.09 | BRL | 0.19 |
| 10 | 19.447 | BRL | 0.07 | BRL | BRL | 0.09 | BRL | 0.25 |
| 12 | 20.119 | 0.05 | 0.08 | BRL | BRL | 0.09 | BRL | 0.27 |
| 24 | 19.319 | BRL | 0.11 | 0.06 | 0.05 | 0.09 | BRL | 0.23 |

| | | | RRT | | | | | |
|---|---|---|---|---|---|---|---|---|
| Time (Hrs) | 0.76 | MW = 557 0.78 | Mino 1.64 | MW = 556 1.67 | MW = 597 1.85 | 1.12 | 1.45 | 1.58 | Total |
| 1 | BRL | BRL | 0.12 | BRL | 0.07 | BRL | 0.09 | 0.06 | 0.60 |
| 4 | BRL | BRL | 0.09 | 0.05 | 0.08 | 0.11 | 0.07 | BRL | 0.70 |
| 8 | BRL | BRL | 0.10 | 0.07 | 0.08 | BRL | 0.07 | 0.06 | 0.66 |
| 10 | 0.05 | BRL | 0.11 | 0.12 | 0.08 | BRL | 0.07 | 0.06 | 0.90 |
| 12 | 0.06 | BRL | 0.10 | 0.06 | 0.09 | BRL | 0.09 | BRL | 0.87 |
| 24 | BRL | BRL | 0.15 | 0.12 | 0.10 | BRL | 0.05 | 0.06 | 1.03 |

| Run #I: Tigecycline 20 mg/mL, (Temperature 5° C., pH 7.9, Oxygen = 1.0 mg/L) | | | | | | | |
|---|---|---|---|---|---|---|---|
| | | | | RRT | | | |
| Time (Hrs) | Strength (mg/mL) | MW = 633 0.12 | MW = 572 0.23 | MW = 601 0.50 | MW = 583 0.55 | 0.58 | 9-Amino 0.64 | Epimer 0.74 |
| 1 | 19.263 | BRL | BRL | BRL | BRL | 0.08 | BRL | 0.19 |
| 4 | 19.361 | BRL | BRL | BRL | BRL | 0.09 | BRL | 0.21 |
| 8 | 19.131 | BRL | BRL | BRL | BRL | 0.06 | BRL | 0.18 |
| 10 | 19.204 | 0.05 | 0.07 | BRL | 0.05 | 0.08 | BRL | 0.29 |
| 12 | 19.151 | 0.06 | 0.07 | BRL | BRL | 0.07 | BRL | 0.26 |
| 24 | 19.242 | BRL | 0.12 | 0.07 | 0.06 | 0.10 | BRL | 0.23 |

| | | | RRT | | | | | |
|---|---|---|---|---|---|---|---|---|
| Time (Hrs) | 0.76 | MW = 557 0.78 | Mino 1.64 | MW = 556 1.67 | MW = 597 1.85 | 1.12 | 1.45 | 1.58 | Total |
| 1 | BRL | BRL | 0.13 | BRL | 0.06 | BRL | 0.09 | BRL | 0.54 |
| 4 | BRL | BRL | 0.10 | 0.05 | 0.09 | BRL | BRL | BRL | 0.54 |

-continued

| Run #I: Tigecycline 20 mg/mL, (Temperature 5° C., pH 7.9, Oxygen = 1.0 mg/L) | | | | | | | | | |
|---|---|---|---|---|---|---|---|---|---|
| 8 | BRL | BRL | 0.09 | 0.05 | 0.08 | BRL | 0.07 | BRL | 0.53 |
| 10 | 0.06 | BRL | 0.08 | 0.08 | 0.10 | BRL | 0.07 | 0.06 | 0.98 |
| 12 | BRL | BRL | 0.08 | BRL | 0.09 | BRL | 0.07 | BRL | 0.71 |
| 24 | BRL | BRL | 0.11 | 0.09 | 0.10 | BRL | 0.08 | BRL | 0.96 |

Tigecycline 20 mg/mL, Run #J, (8° C. temperature, Oxygen = 1.0 mg/mL)

| | | | | | | | RRT | | | | | | |
|---|---|---|---|---|---|---|---|---|---|---|---|---|---|
| Time (Hrs) | Strength (mg/ml) | 0.09 | MW = 572 0.23 | MW = 601 0.50 | MW = 583 0.55 | 0.58 | Epimer 0.74 | MW = 557 0.78 | MW = 528 1.25 | Mino 1.64 | MW = 556 1.67 | MW = 597 1.85 | 1.45 | Total |
| 1 | 19.515 | BRL | BRL | BRL | BRL | 0.06 | 0.20 | BRL | BRL | 0.11 | 0.09 | 0.09 | 0.08 | 0.62 |
| 4 | 19.469 | BRL | 0.09 | 0.05 | 0.08 | 0.06 | 0.22 | BRL | BRL | 0.09 | 0.17 | 0.08 | 0.06 | 0.90 |
| 8 | 19.323 | BRL | 0.14 | 0.09 | 0.08 | 0.06 | 0.22 | BRL | BRL | 0.09 | 0.15 | 0.10 | 0.07 | 1.00 |
| 12 | 19.140 | BRL | 0.20 | 0.12 | 0.09 | 0.06 | 0.24 | BRL | BRL | 0.10 | 0.19 | 0.11 | 0.06 | 1.17 |
| 24 | 19.152 | 0.05 | 0.39 | 0.20 | 0.14 | 0.08 | 0.28 | 0.07 | 0.08 | 0.11 | 0.21 | 0.10 | 0.05 | 1.76 |

Run #K: Tigecycline 20 mg/mL, (Temperature 2° C., pH 8.2, Oxygen = 0.1 mg/L)

| | | | | | | | | RRT | | | | | | | | |
|---|---|---|---|---|---|---|---|---|---|---|---|---|---|---|---|---|
| Time (Hrs) | Strength (mg/mL) | MW = 633 0.12 | MW = 572 0.23 | MW = 601 0.50 | MW = 583 0.55 | 0.58 | 9-Amino 0.64 | Epimer 0.74 | 0.76 | MW = 557 0.78 | Mino 1.64 | MW = 556 1.67 | MW = 597 1.85 | 1.12 | 1.45 | 1.58 | Total |
| 1 | 19.187 | BRL | BRL | BRL | BRL | 0.08 | BRL | 0.16 | BRL | BRL | 0.12 | BRL | 0.08 | BRL | 0.08 | BRL | 0.51 |
| 4 | 19.324 | BRL | BRL | BRL | BRL | 0.08 | BRL | 0.18 | 0.06 | BRL | 0.13 | BRL | 0.08 | BRL | 0.08 | BRL | 0.61 |
| 8 | 19.127 | BRL | BRL | BRL | BRL | 0.07 | BRL | 0.18 | 0.08 | BRL | 0.13 | BRL | 0.08 | BRL | 0.08 | BRL | 0.63 |
| 10 | 20.357 | BRL | BRL | BRL | BRL | 0.07 | BRL | 0.19 | BRL | BRL | 0.15 | BRL | 0.10 | BRL | 0.08 | BRL | 0.59 |
| 12 | 19.956 | BRL | BRL | BRL | BRL | 0.08 | BRL | 0.22 | BRL | BRL | 0.10 | BRL | 0.09 | BRL | 0.09 | BRL | 0.56 |
| 24 | 19.067 | BRL | BRL | BRL | BRL | 0.08 | BRL | 0.17 | BRL | BRL | 0.14 | BRL | 0.08 | BRL | 0.08 | BRL | 0.55 |

Run #L: Tigecycline 20 mg/mL, (Temperature 2° C., pH 7.7, Oxygen = 0.1 mg/L)

| | | | | | | | | RRT | | | | | | | | |
|---|---|---|---|---|---|---|---|---|---|---|---|---|---|---|---|---|
| Time (Hrs) | Strength (mg/mL) | MW = 633 0.12 | MW = 572 0.23 | MW = 601 0.50 | MW = 583 0.55 | 0.58 | 9-Amino 0.64 | Epimer 0.74 | 0.76 | MW = 557 0.78 | Mino 1.64 | MW = 556 1.67 | MW = 597 1.85 | 1.12 | 1.45 | 1.58 | Total |
| 1 | 19.23 | BRL | BRL | BRL | BRL | 0.08 | BRL | 0.17 | BRL | BRL | 0.14 | BRL | 0.07 | BRL | 0.08 | BRL | 0.53 |
| 4 | 19.053 | BRL | BRL | BRL | BRL | 0.08 | BRL | 0.17 | BRL | BRL | 0.15 | BRL | 0.08 | BRL | 0.07 | BRL | 0.54 |
| 8 | 18.988 | BRL | BRL | BRL | BRL | 0.08 | BRL | 0.17 | 0.05 | BRL | 0.13 | BRL | 0.08 | BRL | 0.08 | BRL | 0.60 |
| 10 | 19.424 | BRL | BRL | BRL | BRL | 0.07 | BRL | 0.22 | 0.05 | BRL | 0.13 | BRL | 0.08 | BRL | 0.07 | BRL | 0.62 |
| 12 | 19.448 | BRL | BRL | BRL | BRL | 0.07 | BRL | 0.23 | BRL | BRL | 0.14 | BRL | 0.08 | BRL | 0.07 | BRL | 0.58 |
| 24 | 19.156 | BRL | BRL | BRL | BRL | 0.09 | BRL | 0.21 | BRL | BRL | 0.13 | BRL | 0.09 | BRL | 0.08 | BRL | 0.61 |

Run #M: Tigecycline 20 mg/mL, (Temperature 8° C., pH 7.7, Oxygen = 0.1 mg/L)

| | | | | | | | | RRT | | | | | | | | |
|---|---|---|---|---|---|---|---|---|---|---|---|---|---|---|---|---|
| Time (Hrs) | Strength (mg/ml) | MW = 633 0.12 | MW = 572 0.23 | MW = 601 0.50 | MW = 583 0.55 | 0.58 | 9-Amino 0.64 | Epimer 0.74 | 0.76 | MW = 557 0.78 | Mino 1.64 | MW = 556 1.67 | MW = 597 1.85 | 1.12 | 1.45 | 1.58 | Total |
| 1 | 19.270 | BRL | BRL | BRL | BRL | 0.08 | BRL | 0.20 | 0.06 | BRL | 0.14 | BRL | BRL | BRL | BRL | BRL | 0.47 |
| 4 | 19.340 | BRL | BRL | BRL | BRL | 0.07 | BRL | 0.23 | 0.06 | BRL | 0.08 | BRL | 0.06 | BRL | 0.06 | BRL | 0.57 |
| 8 | 19.238 | BRL | BRL | BRL | BRL | 0.08 | BRL | 0.24 | 0.06 | BRL | 0.11 | BRL | 0.06 | BRL | 0.07 | BRL | 0.62 |

-continued

Run #M: Tigecycline 20 mg/mL, (Temperature 8° C., pH 7.7, Oxygen = 0.1 mg/L)

| Time (Hrs) | Strength (mg/ml) | MW = 633 0.12 | MW = 572 0.23 | MW = 601 0.50 | MW = 583 0.55 | 0.58 | 9-Amino 0.64 | Epimer 0.74 | 0.76 | MW = 557 0.78 | Mino 1.64 | MW = 556 1.67 | MW = 597 1.85 | 1.12 | 1.45 | 1.58 | Total |
|---|---|---|---|---|---|---|---|---|---|---|---|---|---|---|---|---|---|
| 10 | 19.240 | BRL | BRL | BRL | 0.09 | 0.07 | BRL | 0.25 | 0.05 | BRL | 0.09 | (<0.05) | 0.08 | BRL | 0.07 | BRL | 0.71 |
| 12 | 19.240 | BRL | BRL | BRL | 0.07 | BRL | BRL | 0.27 | 0.05 | BRL | 0.12 | 0.07 | 0.08 | BRL | 0.07 | BRL | 0.73 |
| 24 | 19.193 | BRL | BRL | BRL | BRL | 0.08 | BRL | 0.29 | BRL | BRL | 0.09 | (<0.05) | 0.08 | BRL | 0.09 | BRL | 0.62 |

Run #N: Tigecycline 20 mg/mL, (Temperature 8° C., pH 8.2, Oxygen = 0.1 mg/L)

| Time (Hrs) | Strength (mg/ml) | MW = 633 0.12 | MW = 572 0.23 | MW = 601 0.50 | MW = 583 0.55 | 0.58 | 9-Amino 0.64 | Epimer 0.74 | 0.76 | MW = 557 0.78 | Mino 1.64 | MW = 556 1.67 | MW = 597 1.85 | 1.12 | 1.45 | 1.58 | Total |
|---|---|---|---|---|---|---|---|---|---|---|---|---|---|---|---|---|---|
| 1 | 19.343 | BRL | BRL | BRL | BRL | 0.07 | BRL | 0.20 | BRL | BRL | (<0.05) | BRL | 0.11 | BRL | 0.07 | BRL | 0.46 |
| 4 | 19.378 | BRL | BRL | BRL | BRL | 0.07 | BRL | 0.21 | BRL | BRL | 0.10 | BRL | 0.09 | BRL | 0.07 | BRL | 0.54 |
| 8 | 19.275 | BRL | BRL | BRL | BRL | 0.07 | BRL | 0.22 | BRL | BRL | 0.08 | BRL | 0.08 | BRL | 0.08 | BRL | 0.53 |
| 1R | 19.415 | BRL | BRL | BRL | 0.06 | 0.06 | BRL | 0.29 | 0.05 | BRL | 0.08 | BRL | 0.09 | BRL | 0.09 | BRL | 0.72 |
| 12 | 19.382 | BRL | BRL | BRL | BRL | 0.07 | 0.06 | BRL | 0.31 | BRL | BRL | 0.11 | 0.07 | 0.08 | BRL | 0.08 | 0.05 | 0.83 |
| 24 | 19.211 | BRL | BRL | BRL | BRL | 0.06 | BRL | 0.31 | BRL | BRL | 0.13 | 0.07 | 0.11 | BRL | 0.10 | 0.05 | 0.82 |

Tigecycline 20 mg/mL, Run #O, (5° C. Temperature, Oxygen = 0.1 mg/mL)

| Time (Hrs) | Strength (mg/ml) | 0.58 | Epimer 0.74 | 0.76 | Mino 1.64 | MW = 597 1.85 | 1.45 | Total |
|---|---|---|---|---|---|---|---|---|
| 1 | 18.777 | 0.07 | 0.21 | 0.05 | 0.08 | 0.08 | 0.07 | 0.56 |
| 4 | 18.971 | 0.09 | 0.23 | BRL | 0.08 | 0.08 | 0.07 | 0.53 |
| 8 | 19.051 | 0.09 | 0.23 | BRL | 0.06 | 0.09 | 0.09 | 0.55 |
| 12 | 18.722 | 0.07 | 0.24 | BRL | 0.08 | 0.10 | 0.07 | 0.55 |
| 24 | 19.238 | 0.07 | 0.25 | BRL | 0.11 | 0.06 | 0.07 | 0.56 |

What is claimed is:

1. A manufacturing process for the production of tigecycline as a reconstitutable powder having less than 0.9% total degradants comprising the steps:
   a. reducing and maintaining the oxygen level in water for injection to less than or equal to 0.5 ppm while maintaining the temperature at about 2° C. to about 8° C.;
   b. forming a solution of tigecycline in said water of step a at a concentration of about 10 to 50 mg/ml while maintaining said temperature and oxygen level;
   c. filling vials with said solution of step b;
   d. lyophilizing said solution of step c forming 25 mg to 150 mg of reconstitutable powder in a vial;
   e. sealing said vial under nitrogen.

2. The manufacturing process according to claim 1 wherein a solution of tigecycline in step b of the process is at a concentration of about 20 mg/ml.

3. The manufacturing process according to claim 1 wherein in step d of the process 50 mg to 150 mg of reconstitutable powder is in the vial.

4. The process according to claim 1 wherein in step b the solution of tigecycline in water is equal to or greater than 80 L.

5. The process according to claim 1 step a wherein the oxygen level in water is at 0.5 ppm or less by sparging with nitrogen.

6. The process according to claim 5 wherein the oxygen level in water in step a is at about 0.4 ppm or less by sparging with nitrogen.

7. A process according to claim 6 wherein the oxygen level in step a is about 0.1 ppm or less by sparging with nitrogen.

8. The process according to claim 7 wherein the reconstitutable powder has less than 0.5% total degradants.

9. A process according to claim 1 wherein the tigecycline powder available for reconstitution prior to intravenous administration has a shelf life of at least 18 months.

10. The process of claim 1 wherein the process has a total manufacturing hold time for the solution formed in step b of about 13 hours to about 24 hours.

11. The process of claim 10 wherein the process has a total manufacturing hold time for the solution formed in step b of about 13 hours.

* * * * *